(12) United States Patent
McWhirter et al.

(10) Patent No.: US 7,190,441 B1
(45) Date of Patent: Mar. 13, 2007

(54) METHODS AND SYSTEMS FOR PREPARING A SAMPLE FOR THIN FILM ANALYSIS

(75) Inventors: James T. McWhirter, San Jose, CA (US); Liang-Guo Wang, Fremont, CA (US); Hidong Kwak, San Jose, CA (US); Haixing Zou, Sunnyvale, CA (US); Dan Georgesco, San Jose, CA (US); Bernard Lautee, San Jose, CA (US); Jennming James Chen, Campbell, CA (US); Gary R. Janik, Palo Alto, CA (US); Patrick M. Maxton, San Jose, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 209 days.

(21) Appl. No.: 11/021,555

(22) Filed: Dec. 22, 2004

Related U.S. Application Data (60) Provisional application No. 60/532,693, filed on Dec. 23, 2003.

(51) Int. Cl.
*G01N 1/00* (2006.01)
(52) U.S. Cl. ...................................... 356/36
(58) Field of Classification Search .................... 356/36
See application file for complete search history.

(56) References Cited

U.S. PATENT DOCUMENTS

| | | | |
|---|---|---|---|
| 5,485,091 A | 1/1996 | Verkuil | |
| 5,608,526 A | 3/1997 | Piwonka-Corle et al. | |
| 5,747,813 A | 5/1998 | Norton et al. | |
| 6,261,853 B1 | 7/2001 | Howell et al. | |
| 6,325,078 B2 | 12/2001 | Kamieniecki | |
| 6,734,968 B1 | 5/2004 | Wang et al. | |
| 6,771,735 B2 | 8/2004 | Janik et al. | |
| 7,110,113 B1 * | 9/2006 | Janik et al. | 356/369 |
| 2003/0137662 A1 | 7/2003 | Janik et al. | |

* cited by examiner

*Primary Examiner*—Gregory J. Toatley, Jr.
*Assistant Examiner*—Roy M. Punnoose
(74) *Attorney, Agent, or Firm*—Baker & McKenzie LLP (57) ABSTRACT

Methods and systems for preparing a sample for thin film analysis are provided. One system includes an energy beam source configured to generate an energy beam. The system also includes an energy beam delivery subsystem configured to direct the energy beam to a sample and to modify the energy beam such that the energy beam has a substantially flat-top profile on the sample. The energy beam removes a portion of a contaminant layer on the sample to expose an analysis area of a thin film on the sample. One method includes generating an energy beam and modifying the energy beam such that the energy beam has a substantially flat-top profile. The method also includes directing the energy beam to a sample. The energy beam removes a portion of a contaminant layer on the sample to expose an analysis area of a thin film on the sample.

20 Claims, 5 Drawing Sheets

METHODS AND SYSTEMS FOR PREPARING A SAMPLE FOR THIN FILM ANALYSIS

This application claims priority to U.S. Provisional Application No. 60/532,693 entitled "Method for Maximizing Spatial Uniformity in Fiber Coupled Light Delivery Systems," filed Dec. 23, 2003, which is incorporated by reference as if fully set forth herein.

BACKGROUND OF THE INVENTION

1. Field of the Invention

The present invention relates to methods and systems for preparing a sample for thin film analysis. Certain embodiments relate to methods that include modifying an energy beam such that the energy beam has a substantially flat-top profile and directing the energy beam to a sample to remove a contaminant layer on the sample.

2. Description of the Related Art

The following description and examples are not admitted to be prior art by virtue of their inclusion in this section.

As the dimensions of semiconductor devices continue to shrink, accurate and efficient characterization of the components forming those devices becomes more critical. Typically, the manufacturing process for modern semiconductor devices includes the formation of a number of layers or "thin films" on a silicon wafer. The thin films can include oxide, nitride, and/or metal layers, among others. To ensure proper performance of the finished semiconductor devices, the thickness and composition of each thin film formed during the manufacturing process must be tightly controlled.

Modern thin films have reached the point where the accuracy and reproducibility of thin film measurements can be limited by contamination on the surface of the thin film. For example, the absorption of water and other vapors onto the thin film can create a contaminant layer that adversely affects thin film analysis techniques such as optical ellipsometry, optical reflectometry, grazing-incidence x-ray reflectometry (GXR), x-ray fluorescence (XRF), electron microprobe analysis (EMP), and non-contact electrical analysis, all of which operate by directing a probe beam (optical, x-ray, electron, or corona discharge) at the surface of the thin film to be measured. The contaminant layer can also interfere with measurement techniques that physically contact the surface of the thin film, such as contact-based electrical analysis (e.g., spreading resistance analysis).

Figure 1A:
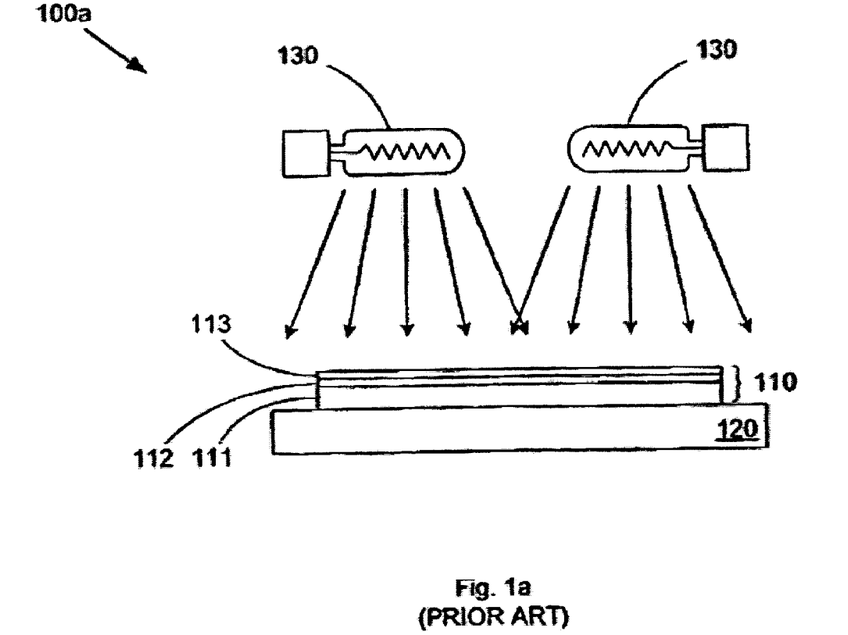
FIGS. 1a and 1b show conventional wafer cleaning systems.

Conventional methods for cleaning thin films involve heating the entire wafer in an oven to a temperature of about 300° C. to vaporize any contaminant layer. FIG. 1a shows conventional oven-based wafer cleaning system 100a used to prepare wafer 110 for thin film analysis, as described in U.S. Pat. No. 6,325,078 to Kamieniecki, which is incorporated by reference as if fully set forth herein. Wafer 110 includes thin film layer 112 formed on silicon substrate 111, and contaminant layer 113 formed on the surface of thin film layer 112. Wafer cleaning system 100a includes wafer stage 120 and multiple heat lamps 130. Wafer stage 120 positions wafer 110 under heat lamps 130, where thermal radiation from heat lamps 130 heats wafer 110 to vaporize contaminant layer 113. It is believed that this cleaning process is aided by the optical photons from heat lamps 130 effectively breaking bonds between contaminant layer 113 and thin film layer 112.

Figure 1B:
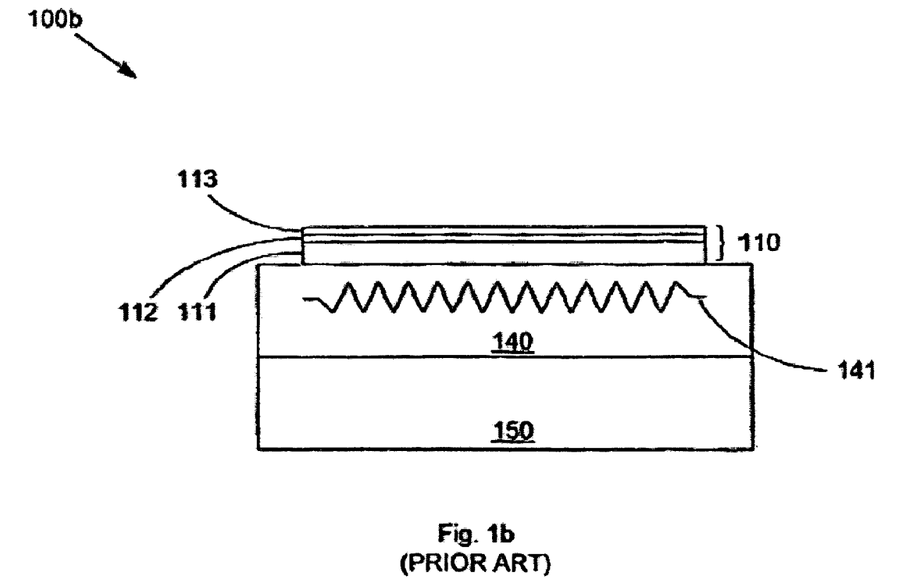

FIG. 1b shows another conventional wafer cleaning system 100b used to prepare wafer 110 for thin film analysis, as described in U.S. Pat. No. 6,261,853 to Howell et al., which is incorporated by reference as if fully set forth herein. Just as described with respect to FIG. 1a, wafer 110 includes thin film layer 112 formed on silicon substrate 111 and contaminant layer 113 formed on the surface of thin film layer 112. Cleaning system 100b incorporates stage 140 that includes heating element 141. Heat generated by heating element 141 is conducted through stage 140 into wafer 110, thereby providing the heating required to vaporize contaminant layer 113. Heat exchanger 150 coupled to stage 140 captures excess heat from heating element 141, thereby minimizing undesirable heating of cleaning system 100b itself and the surrounding environment.

Although wafer cleaning systems 100a and 100b use different thermal energy sources (i.e., heat lamps 130 and heating element 141, respectively), both systems perform a bulk heating operation to remove contaminant layer 113. The large thermal control components (e.g., lamps, heated stages, heat exchangers, etc.) typically used for bulk wafer heating undesirably increase the cleanroom space required for these conventional cleaning systems. Further exacerbating the problem of excess equipment size, conventional cleaning systems are sometimes stand-alone units used in conjunction with a thin film analysis tool. Therefore, conventional cleaning systems can significantly increase the total footprint required for a complete thin film analysis system. The use of a separate cleaning system also has an adverse effect on throughput, as time must be spent transferring the wafer to and from the cleaning system. In addition, contaminants can redeposit on the cleaned wafer when it is transferred from the cleaning system to the film analysis tool.

In an attempt to somewhat alleviate these equipment size and recontamination problems, attempts have been made to combine wafer cleaning and measurement capabilities in a single tool. For example, the aforementioned U.S. Pat. No. 6,261,853 to Howell et al. describes integrating cleaning system 100b with an existing metrology tool (Opti-Probe 5240 from Therma-Wave, Inc.). Also, the Quantox XP tool from KLA-Tencor integrates a wafer cleaning system similar to cleaning system 100b with a non-contact electrical film measurement system. However, any bulk wafer heating system must still incorporate the aforementioned (large) thermal control components. Furthermore, even if a combined system is used, the bulk heating operation can significantly degrade overall wafer processing throughput. Several seconds are required to heat the wafer to the temperature required for removal of the contaminant layer, and another several seconds are required to cool down the wafer after cleaning. Any wafer handling operations that must be performed during and after the cleaning operation (e.g., transferring the wafer from the cleaning system to the thin film analysis system) further reduce the throughput.

Accordingly, it is desirable to provide an efficient wafer cleaning system for thin film measurement systems that does not require lengthy heating and cooling times, does not require dedicated wafer handling steps, and does not require a substantial footprint.

SUMMARY OF THE INVENTION

The present invention provides localized contaminant layer removal from a thin film surface, thereby enabling accurate and repeatable analysis of the thin film by a measurement tool. By using a concentrated energy beam to clean only the portion of the thin film to be measured by the measurement tool, the thin film analysis can be performed without the long heating and cooling times associated with conventional cleaning systems. Furthermore, the compact components used in an energy beam-based cleaning system can be incorporated into the thin film measurement tool itself, thereby eliminating any delays related to transferring the wafer to and from a stand-alone cleaning system. This integration also minimizes the total footprint required for a thin film analysis system, and since the wafer can be cleaned and analyzed in the same process chamber, redeposition of contaminants on the cleaned portion of the wafer can be prevented. In order to improve the cleaning of the substrate, and avoid damaging the substrate, a substantially flat-top profile is used for the energy beam. This substantially flat-top profile may be provided as described herein.

A thin film analysis system in accordance with an embodiment includes an energy beam source, an analysis module, and a stage. The stage holds a test sample (such as a wafer) that includes a thin film layer to be measured by the analysis module. The analysis module can include any thin film analysis system or systems, including a single-wavelength ellipsometer (SWE, such as described in co-owned U.S. Pat. No. 6,734,968 to Wang et al.), a spectroscopic ellipsometer (SE, such as described in co-owned U.S. Pat. No. 5,608,526 to Piwonka-Corle et al.), a reflectometer (such as described in co-owned U.S. Pat. No. 5,747,813 to Norton et al.), a non-contact electrical measurement system (such as described in co-owned U.S. Pat. No. 5,485,091 to Verkuil), a GXR system (such as described in co-owned, U.S. Pat. No. 6,771,735, a contact-based electrical measurement system, an XRF system, and/or an EMP system. Each of these patents and patent application are incorporated by reference as if fully set forth herein. More generally, this cleaning system can be used with any sort of inspection or metrology system used in the production of semiconductor devices. According to an embodiment, the energy beam source is incorporated into a conventional thin film analysis tool, thereby minimizing the total footprint of the thin film analysis system.

The energy beam source is configured to direct an energy beam at a contaminant layer on the surface of the thin film layer. The energy beam heats a portion of the contaminant layer until that portion of the contaminant layer is vaporized. This process can be aided by direct photon excitation of the bonds between the contaminant layer and the thin film layer. The area of the thin film layer exposed by this cleaning operation can then be analyzed by the analysis module. The size of this analysis area required by the analysis module for performance of the thin film analysis can be used to determine the minimum required power and size of the energy beam. By minimizing the power and size of the energy beam, the risk of damage to the test sample is small. This risk of damage can be further reduced by performing the cleaning and measuring operations at non-functional regions of the test sample. According to an embodiment, the energy beam source can include a laser, such as a Q-switched pulsed laser. In a different embodiment, the energy beam source can include a continuous (cw) laser. According to another embodiment, the energy beam source can include a flashlamp with appropriate focusing optics.

According to an embodiment, a probe beam generated by the analysis module (e.g., a low-power laser beam, a white light beam, a corona discharge, an x-ray beam, etc.) is directed at the same location on the test sample as the energy beam produced by the energy beam source. Alternatively, a physical probe structure (e.g., a four-point probe in a spreading resistance tool) can be aimed at the same location on the test sample as the energy beam produced by the energy beam source. Consequently, the test sample does not need to be moved between the cleaning and measurement operations, thereby maximizing analysis throughput. Furthermore, because the measurement operation can be performed immediately after the cleaning operation, the chances of the cleaned portion of the thin film layer (i.e., the analysis area) being recontaminated before the measurement operation are minimized.

According to another embodiment, the probe beam (or probe structure) from the analysis module and the energy beam are directed at different locations on the test sample. The test sample (and/or the analysis module) is then repositioned after the cleaning operation to align the probe beam (or probe structure) with the analysis area of the thin film layer. This allows the focusing optics or probe structure of the analysis module to be kept out of the vicinity of the portion of the contaminant layer being vaporized, thereby minimizing the risk of any contaminant redeposition on the measurement focusing optics or probe structure. In each of the aforementioned embodiments, a substantially flat-top profile of the energy beam may be employed.

In a preferred embodiment, certain novel methods are used to generate the substantially flat-top profile. Optical fibers are often used to deliver light from an optical source to a surface, which is typically placed at the image plane of an optical focus system. The applications in which optical fibers are used vary and include optical cleaning, illumination for optical inspection, metrology measurements, pattern marking, thin film growth by ablation, etc. Multi-mode fibers are often used in such applications, when a so-called "flat-top" intensity profile is desired. A multi-mode optical fiber can have an intensity profile at the exit face of the fiber that is roughly constant across the surface (i.e., a substantially flat-top profile), and a focus system can image this profile onto the surface of interest. However, when using coherent optical sources (such as a laser), the exit-face intensity profile has a characteristic speckle pattern, due to the propagation of coherent light through the fiber in discrete spatial modes, which are characteristic of the fiber's optical properties. This speckle pattern results in an intensity profile at the exit face that has sharp intensity fluctuations. Increasing the diameter of the fiber results in more available spatial modes, and the more spatial modes that are populated, the more uniform the intensity profile will be. However, efficiently coupling the light into the fiber so as to fully populate the available spectrum of spatial modes is often difficult.

In contrast, the methods and systems described herein may efficiently couple an energy beam into the spatial mode spectrum of a fiber to produce an energy beam that has a substantially flat-top profile, and in a more preferred embodiment, does so without having to resort to static stress-induced mode mixing (e.g., bending or twisting the fiber).

One embodiment relates to a system configured to prepare a sample for thin film analysis. The system includes an energy beam source configured to generate an energy beam. The system also includes an energy beam delivery subsystem that is configured to direct the energy beam to the sample and to modify the energy beam such that the energy beam has a substantially flat-top profile on the sample. The substantially flat-top profile has an approximately constant intensity across the profile of the energy beam. The energy beam is configured to remove a portion of a contaminant layer on the sample to expose an analysis area of a thin film on the sample.

In one embodiment, the energy beam source may include a laser. The energy beam delivery subsystem may include a multi-mode optical fiber. In some embodiments, the energy beam delivery subsystem may include an optical fiber that is tapered along a length of the optical fiber. In one such embodiment, the energy beam delivery subsystem may also include coupling optics configured to couple the energy beam into the optical fiber. The numerical aperture of the coupling optics may be less than an input numerical aperture of the optical fiber.

In another embodiment, the energy beam delivery subsystem may include an optical fiber coupled to a modulation device. The modulation device is configured to modulate a position of the optical fiber. In one such embodiment, the optical fiber may include an optical fiber that is tapered along a length of the optical fiber. However, in another such embodiment, the optical fiber may be a non-tapered optical fiber.

In additional embodiments, the energy beam delivery subsystem may include an optical fiber and a modulation device. In this embodiment, the modulation device is configured to modulate a position of the energy beam directed to the optical fiber. In a different embodiment, the energy beam delivery subsystem may include an optical fiber coupled to coupling optics. The coupling optics are configured to couple the energy beam into the optical fiber. In this embodiment, the coupling optics include an optical diffuser.

In further embodiments, the system may also include a detector coupled to a stage (e.g., the stage configured to support the sample). The detector is configured to monitor intensity of the energy beam as a function of position across the profile. In one such embodiment, the detector may include a single sensing element. In another such embodiment, the detector may be configured to monitor focus of the energy beam on the sample. In another preferred embodiment, the system may include a thin film analysis subsystem. The thin film analysis subsystem and the energy beam delivery subsystem are coupled to a common stage. Each of the embodiments of the system described above may be further configured as described herein.

One method for preparing a sample for thin film analysis includes generating an energy beam. The method also includes modifying the energy beam such that the energy beam has a substantially flat-top profile. The substantially flat-top profile has an approximately constant intensity across the profile of the energy beam. In addition, the method includes directing the energy beam to the sample. The energy beam is configured to remove a portion of a contaminant layer on the sample to expose an analysis area of a thin film on the sample.

In one embodiment, modifying the energy beam includes physically modulating a position of an optical fiber along which the energy beam is traveling. In a different embodiment, modifying the energy beam includes modulating a position of the energy beam directed to an optical fiber. In addition, the optical fiber may be a tapered optical fiber. In some embodiments, the method may include monitoring intensity of the energy beam as a function of position across the profile. The sample is disposed on a stage during generation of the energy beam, modification of the energy beam, and delivery of the energy beam. In one such embodiment, the method may also include performing the thin film analysis of the analysis area while the sample is disposed on the stage. Each of the embodiments of the method described above may include any other step(s) described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "sample" generally refers to a wafer. As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include only the substrate such as a virgin wafer. Alternatively, a wafer may include one or more layers formed upon a substrate. For example, such layers may include, but are not limited to, a resist, a dielectric material, and a conductive material. A resist includes any material that may be patterned by an optical lithography technique, an e-beam lithography technique, or an X-ray lithography technique. Examples of a dielectric material include, but are not limited to, silicon dioxide, silicon nitride, silicon oxynitride, and titanium nitride. Additional examples of a dielectric material include "low-k" dielectric materials such as Black Diamond™ which is commercially available from Applied Materials, Inc., Santa Clara, Calif., and CORAL™ commercially available from Novellus Systems, Inc., San Jose, Calif., "ultra-low k" dielectric materials such as "xerogels," and "high-k" dielectric materials such as hafnium oxide. In addition, examples of a conductive material include, but are not limited to, aluminum, polysilicon, and copper.

One or more layers formed on a wafer may be patterned or unpatterned. For example, a wafer may include a plurality of dies having repeatable pattern features. Formation and processing of such layers of material may ultimately result in completed semiconductor devices. As such, a wafer may include a substrate on which not all layers of a complete semiconductor device have been formed or a substrate on which all layers of a complete semiconductor device have been formed. The term "semiconductor device" is used interchangeably with the term "integrated circuit."

The sample may further include at least a portion of a thin-film head die formed on a wafer, at least a portion of a micro-electro-mechanical system (MEMS) device formed on a wafer, flat panel displays, magnetic heads, magnetic and optical storage media, and at least a portion of other components that may include photonics and optoelectronic devices such as lasers, waveguides and other passive components processed on wafers, print heads, and bio-chip devices processed on wafers. In addition, a sample may include a "reticle" or a "mask." Many different types of reticles are known in the art, and the term "reticle" as used herein is intended to encompass all known types of reticles.

Figure 2A:
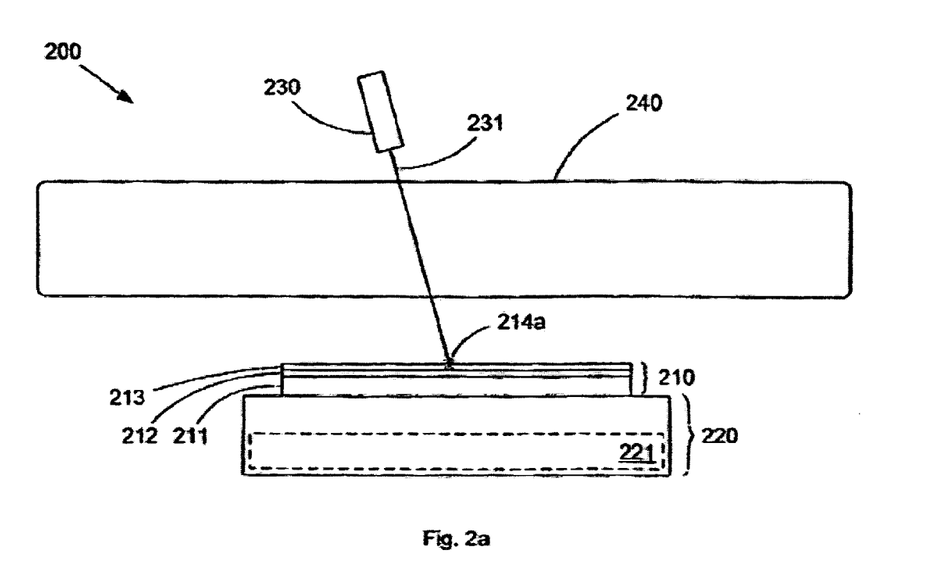
FIGS. 2a and 2b show a thin film analysis system in accordance with an embodiment.

FIG. 2a shows thin film analysis system 200 in accordance with an embodiment. Analysis system 200 includes stage 220, energy beam source 230, and analysis module 240. Stage 220 holds test sample 210 that includes thin film layer 212 formed on substrate 211. Substrate 211 can include any structure on which thin film layer 212 can be formed, including a single-layer structure (such as a silicon wafer) or a multi-layer structure (such as an additional thin film layer or layers formed on a silicon wafer). Substrate 211 may also include any of the samples described above. Test sample 210 also includes contaminant layer 213 formed on the surface of thin film layer 212. Contaminant layer 213 can include any unwanted material on the surface of thin film layer 212.

An analysis operation performed using analysis system 200 actually includes two steps: a cleaning operation and a measurement operation. During the cleaning operation, a small portion of contaminant layer 213 is removed. The exposed portion (i.e., analysis area) of thin film layer 212 is then analyzed during the measurement operation. According to an embodiment, the position of stage 220 can be shifted relative to energy beam source 230 and analysis module 240 to enable thin film analysis at multiple locations on test sample 210. According to one such embodiment, stage 220 can include positioning mechanism 221 to enable this positional shifting.

To perform a cleaning operation, energy beam source 230 directs energy beam 231 at spot 214a on contaminant layer 213. Energy beam 231 is configured to remove a portion of contaminant layer 213 by heating contaminant layer 213 directly or by heating the underlying portion of thin film layer 212 or substrate 211. The portion of contaminant layer 213 heated in this manner is eventually vaporized, thereby exposing the underlying portion of thin film layer 212. As noted previously, this removal process can be aided by other mechanisms besides heating, including the direct stimulation of the bonds between contaminant layer 213 and thin film layer 212 by photons from energy beam 231.

Because the heating from energy beam source 230 is confined to a localized area, the cleaning operation can be performed very rapidly, which minimizes any impact on analysis throughput. The potential for damage to underlying thin film layer 212 and/or substrate 211 is minimal because only a small portion of test sample 210 is heated. This risk of damage can be further reduced by performing the cleaning operation on non-functional regions of test sample 210 (e.g., regions such as scribe lines that will not be part of the functional portion(s) of the final devices to be made from test sample 210).

The amount of contaminant layer 213 to be removed depends on the measurement requirements of analysis module 240. Modern thin film analysis tools generally require an analysis area of at least 20 µm×20 µm. Therefore, at least a 20 µm×20 µm portion of contaminant layer 213 would need to be removed for such systems. However, to ensure that the entire analysis area is uniformly cleaned, a larger portion of contaminant layer 213 could be removed.

In one embodiment, energy beam source 230 could be a continuous laser (cw). According to another embodiment, energy beam source 230 could include a pulsed laser. For example, contaminant layer 213 could include a 5 angstrom thick layer of water and organic materials (which is similar to contamination layers often formed on modern thin film layers during production). A number of pulses or even a single pulse from a 5–100 µJoule laser having a 1–1000 ns pulse duration could then heat the desired portion of contaminant layer 213 to between roughly 300° C. to 1000° C., which is a temperature range sufficient to vaporize that portion of contaminant layer 213. According to another embodiment, energy beam source 230 could include a Q-switched laser delivering a relatively high peak power, such as a frequency-doubled or tripled YAG (yttrium aluminum garnet) laser operating at a wavelength of 532 nm or 355 nm, respectively. According to another embodiment, other types of pulsed lasers operating at different wavelengths might be used including pulsed diode or alexandrite lasers. According to another embodiment, a continuous laser, such as an argon-ion laser, could be externally modulated (such as with an acousto-optic or electro-optic modulator) to produce a pulse. Alternatively, a continuous laser could be used without modulation. According to another embodiment, energy beam source 230 could be coupled to focusing optics such as an optical fiber and a lens system to deliver a beam of the desired size and energy to spot 214a from a remote location, i.e., the optical fiber could transmit energy beam 231 from a remote beam generator to spot 214a. Several embodiments of such an energy beam delivery subsystem are described further herein. According to another embodiment, energy beam source 230 could include a flashlamp coupled to focusing optics to direct the high intensity light to the desired area on contaminant layer 213.

Figure 2B:
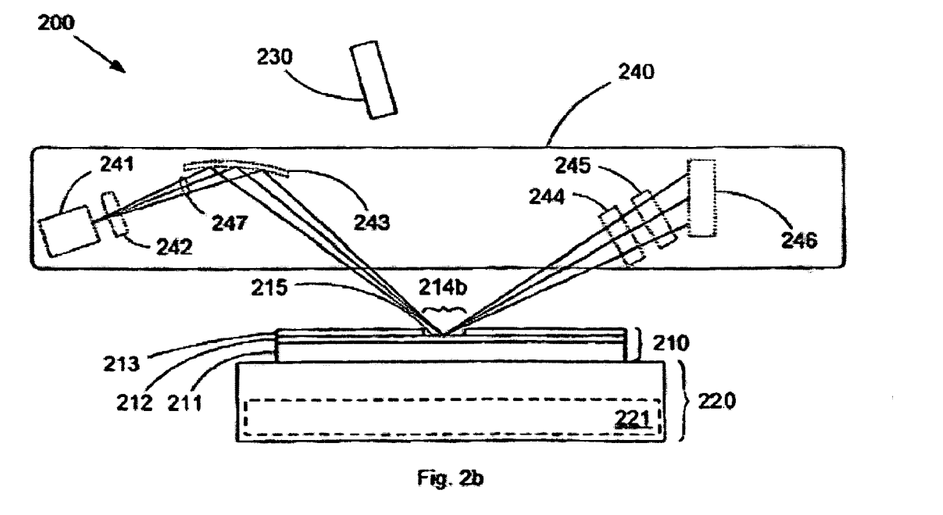

Once the cleaning operation is completed, the measurement operation can be performed. Because test sample 210 does not need to be transferred to a different tool or process chamber, the measurement operation can be performed immediately following the cleaning operation, so that the chances of recontamination of the exposed portion (analysis area) of thin film layer 212 are minimized. For explanatory purposes, FIG. 2b depicts analysis module 240 as including xenon lamp 241, rotating polarizer 242, focusing mirror 243, fixed polarizer 244, spectrometer 245, and CCD detector 246 for performing spectroscopic ellipsometry analysis. However, analysis module 240 can include a system or systems for any type of analysis that would benefit from removal of contaminant layer 213, including SWE, SE, reflectometry (optical or x-ray), GXR, XRF, EMP, and noncontact or contact-based electrical analysis, among others. Note that analysis system 200 can include a conventional thin film analysis system to which energy beam source 230 is added, thereby minimizing the footprint of analysis system 200.

As indicated in FIG. 2b, contaminant layer 213 includes opening 214b formed by the laser heating of spot 214a during the preceding cleaning operation (as shown in FIG. 2a). The measurement operation, therefore, can be performed directly on thin film layer 212 through opening 214b. Xenon lamp 241 directs a diverging light beam 247 through rotating polarizer 242 at focusing mirror 243, which reflects and focuses beam 247 through opening 214b in contaminant layer 213 onto analysis area 215 on thin film layer 212. Light beam 247 is reflected by thin film layer 212 as a diverging beam, which passes through fixed polarizer 244 and spectrometer 245 before being measured by CCD detector 246 to determine the thickness of thin film layer 212.

In this manner, a localized cleaning operation can be efficiently combined with a measurement operation to ensure accurate and repeatable thin film analyses. Because both energy beam 231 and the probe beam from analysis module 240 (here represented by light beam 247) are simultaneously directed at substantially the same location on test sample 210, the position of test sample 210 does not have to be adjusted between cleaning and measurement operations. Therefore, the measurement operation can be performed immediately after the cleaning operation to ensure that a new contaminant layer is not reformed over analysis area 215.

Figure 3A:
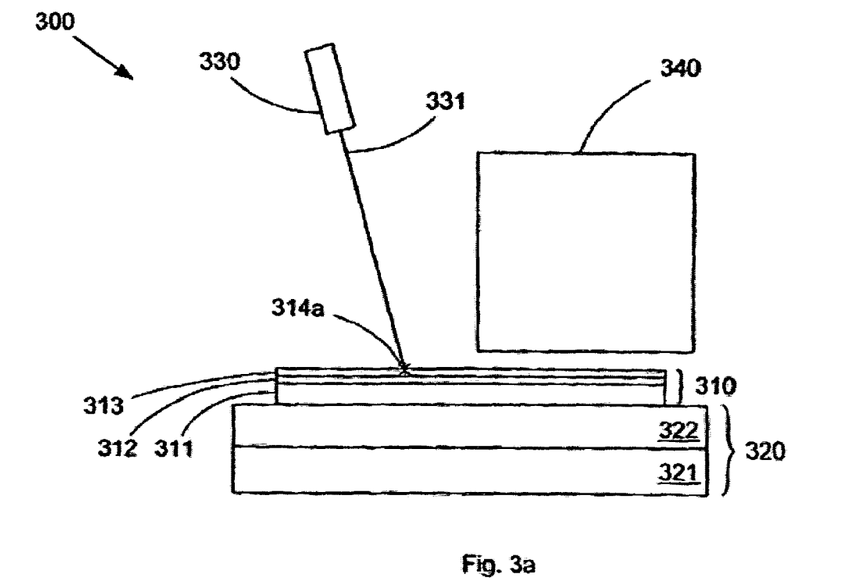
FIGS. 3a and 3b show a thin film analysis system in accordance with another embodiment.

FIG. 3a shows thin film analysis system 300 in accordance with another embodiment. Analysis system 300 includes stage 320, energy beam source 330, and analysis module 340. Stage 320 includes positioning mechanism 321 and platform 322. Positioning mechanism 321 allows the position of platform 322 to be shifted relative to energy beam source 330 and analysis module 340. Platform 322 holds test sample 310 that includes thin film layer 312 formed on substrate 311. Substrate 311 can include any material on which thin film layer 312 can be formed, including a single material (such as a silicon wafer) or a plurality of materials (such as an additional thin film layer or layers formed on a silicon wafer). The substrate may also include any of the samples described above. Test sample 310 also includes contaminant layer 313 formed on the surface of thin film layer 312. Contaminant layer 313 can include any unwanted material on the surface of thin film layer 312.

Unlike in analysis system 200 shown in FIGS. 2a and 2b, energy beam source 330 and analysis module 340 are not simultaneously focused at the same location on test sample 310. Consequently, an analysis operation performed using analysis system 300 actually includes three steps: a cleaning operation, a positioning operation, and a measurement operation. During the cleaning operation, a small portion of contaminant layer 313 is removed by the energy beam from energy beam source 330. Then, during the positioning operation, test sample 310 is positioned such that the probe beam of analysis module 340 is aligned with the portion of thin film layer 312 exposed during the cleaning operation. The exposed portion of thin film layer 312 can then be analyzed by analysis module 340 during the measurement operation.

To perform a cleaning operation, energy beam source 330 directs energy beam 331 at point 314a on contaminant layer 313. Energy beam 331 is configured to remove a portion of contaminant layer 313 by heating contaminant layer 313 directly or by heating the underlying portion of thin film layer 312 or substrate 311. The portion of contaminant layer 313 heated in this manner is vaporized, thereby exposing the underlying portion of thin film layer 312.

Because the heating from energy beam source 330 is confined to a localized area, the cleaning operation can be performed very rapidly, which minimizes any impact on analysis throughput. The potential for damage to underlying thin film layer 312 and/or substrate 311 is minimal because only a small portion of test sample 310 is heated. This risk of damage can be further reduced by performing the cleaning operation on nonfunctional regions of test sample 310.

The amount of contaminant layer 313 to be removed depends on the measurement requirements of analysis module 340. As described previously, modern thin film analysis tools generally take measurements within a roughly 20 μm×20 μm spot. Accordingly, energy beam source 330 could include a 5–100 μJoule pulsed laser with a pulse duration of 1–1000 ns, which would be capable of vaporizing a 20 μm×20 μm (or slightly larger) portion of a 5 angstrom thick contaminant layer (contaminant layer 313) of adsorbed water vapor. According to an embodiment, energy beam source 330 could include a Q-switched laser delivering a relatively high peak power, such as a frequency-doubled or tripled YAG (yttrium aluminum garnet) laser operating at a wavelength of 532 nm or 355 nm, respectively. In another embodiment, energy beam source 330 could be a continuous (cw) laser. According to another embodiment, energy beam source 330 could be coupled to focusing optics such as an optical fiber and a lens system to deliver a beam of the desired size and energy to spot 314a from a remote location, i.e., the optical fiber could transmit energy beam 331 from a remote beam generator to spot 314a. Several embodiments of an energy beam delivery subsystem are further described herein. According to another embodiment, energy beam source 330 could include a flashlamp coupled to focusing optics to direct the high intensity light to the desired area on contaminant layer 213.

Figure 3B:
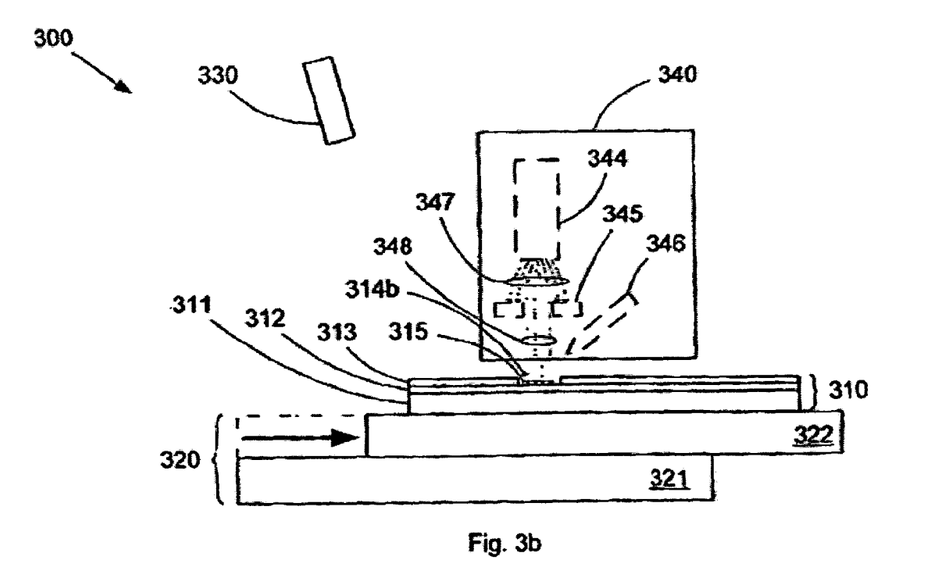

As indicated in FIG. 3b, the cleaning operation creates opening 314b in contaminant layer 313 (at spot 314a shown in FIG. 3a), thereby exposing analysis area 315 of thin film layer 312. A positioning operation then aligns analysis area 315 with the probe beam from analysis module 340, in this case electron beam (e-beam) 348. This positioning operation is performed by positioning mechanism 321, which shifts platform 322 relative to analysis module 340 (as indicated by the phantom lines). While a lateral shift is indicated in FIG. 3b, any other type of positioning motion could be used, including a rotational or vertical shift. In this manner, the probe beam focusing optics in analysis module 340 can be maintained at a distance from the portion of contaminant layer 313 being removed during the cleaning operation (point 314a shown in FIG. 3a). This in turn minimizes the risk of any of vaporized contaminant layer 313 redepositing on the probe beam focusing optics or probe structure of analysis module 340.

After the positioning operation is completed, the measurement operation can be performed by analysis module 340. Because test sample 310 does not have to be transferred to a different tool or process chamber, there is little chance of recontamination of analysis area 315. For explanatory purposes, FIG. 3b depicts analysis module 340 as including corona discharge gun 344, charge mask 345, and vibrating probe 346 for performing non-contact electrical analysis, as described in co-owned U.S. Pat. No. 5,485,091 to Verkuil, which is incorporated by reference as if fully set forth herein. However, analysis module 340 can include a system or systems for any type of analysis that would benefit from removal of contaminant layer 313, including SWE, SE, reflectometry, GXR, XRF, EMP, and non-contact or contact-based electrical analysis, among others. Note that analysis system 300 can include a conventional thin film analysis system to which energy beam source 330 is added, thereby minimizing the footprint of analysis system 300.

As indicated in FIG. 3b, the measurement operation is performed through opening 314b formed in contaminant layer 313 during the preceding cleaning operation. Corona discharge gun 344 produces corona discharge 347 that is shaped into negative charge beam 348 by charge mask 345. Negative charge beam 348 deposits a negative charge onto analysis area 315 through opening 314b in contaminant layer 313. The resulting change in surface potential can then be measured by vibrating probe 346 to determine the thickness and electrical properties of thin film layer 312.

In this manner, a localized cleaning operation can be efficiently combined with a measurement operation to ensure accurate and repeatable thin film analyses. By allowing the position of test sample 310 to be shifted between the cleaning and measurement operations, energy beam 331 and the probe beam of analysis module 340 (here represented by negative charge beam 348) do not need to be focused at the same location on test sample 310. Therefore, the focusing optics of analysis module 340 can be distanced from any contamination released during the cleaning operation.

The systems and methods described herein, if desired, may be employed by using the laser cleaning step in an interleaved manner, as further described in commonly assigned pending U.S. patent application Ser. No. 10/616,064 by Janik et al., filed Jul. 8, 2003. Alternatively, the systems and methods described herein can be used in conjunction with the apparatus and methods described in commonly assigned pending U.S. patent application Ser. No. 10/056,271 by Janik et al., filed on Jan. 23, 2002. These applications are hereby incorporated by reference for all purposes and as if fully set forth herein.

Figure 4:
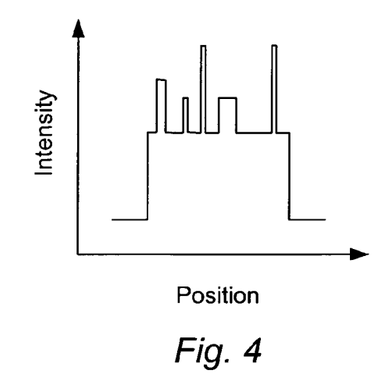
FIG. 4 is a plot illustrating a cross-sectional view of a profile of an energy beam without modification.

In each of the aforementioned embodiments, it is desirable for the energy beam to have a substantially flat-top profile. For instance, as shown in FIG. 4, under normal circumstances, the energy beam will have a profile that has varying intensity as a function of position. In particular, when using coherent optical sources (such as a laser) coupled with a multi-mode optical fiber, the intensity profile of the energy beam exiting the optical fiber has a characteristic speckle pattern, due to the propagation of coherent light through the fiber in discrete spatial modes, which are characteristic of the fiber's optical properties. This speckle pattern results in an intensity profile at the exit face that has sharp intensity fluctuations, as shown in FIG. 4.

The variations in the intensity of the energy beam across the beam profile are particularly disadvantageous for the systems and methods described herein. For example, the energy beam is used, as described further above, to heat or otherwise promote removal of a portion of a contaminant layer on a sample. In this manner, when the energy beam has a profile in which intensity varies as a function of position, the contaminant layer will be heated or otherwise removed in a non-uniform manner. Non-uniform removal of the contaminant layer in the analysis area obviously can have a substantially adverse effect on the accuracy of the measurements performed using a thin film analysis subsystem.

Figure 5:
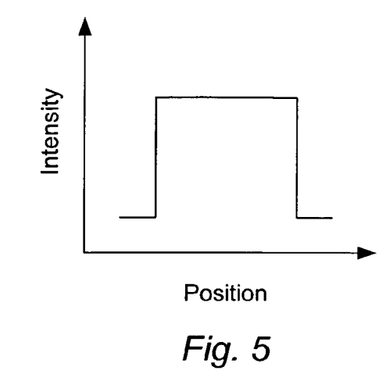
FIG. 5 is a plot illustrating a cross-sectional view of a profile of an energy beam after modification according to embodiments described herein.

Accordingly, it would be advantageous for the systems and methods described herein if the energy beam used for localized contaminant layer removal has a substantially flat-top profile. In other words, it would be advantageous for the energy beam to have an approximately constant intensity across the profile of the energy beam. As shown in FIG. 5, one such substantially flat-top profile has a step-function type shape. In this manner, the energy beam intensity falls off dramatically proximate the outer edges of the energy beam profile and is substantially constant across the positions within the energy beam profile. Although the substantially flat-top profile is shown in FIG. 5 to have no variation in intensity across the profile, it is to be understood that a "substantially flat-top profile" as described herein may have some relatively negligible variation in intensity across the profile due to, for example, the fact that a perfect step function profile will be nearly impossible to obtain. However, in any case, a substantially flat-top profile as described herein will provide substantially uniform heating or otherwise facilitating removal of the contaminant layer in the analysis area thereby substantially improving the accuracy with which measurements may be made in the analysis area.

Such a substantially flat-top profile can be achieved in a variety of ways. Generally, a system configured to prepare a sample for thin film analysis includes an energy beam source configured to generate an energy beam. The system also includes an energy beam delivery subsystem configured to direct the energy beam to the sample and to modify the energy beam such that the energy beam has a substantially flat-top profile on the sample. The energy beam is configured to remove a portion of a contaminant layer on the sample to expose an analysis area of a thin film on the sample, as described above. This general system embodiment may be further configured as described herein. For example, the system may include a thin film analysis subsystem. The thin film analysis subsystem and the energy beam delivery subsystem are preferably coupled to a common stage as described further herein.

In one example, diffractive optics can be used to produce the energy beam profile. Alternatively, a relatively wide energy beam could be produced with a Gaussian profile, followed by a narrow aperture to shape the beam and to allow only the relatively flat center portion of the Gaussian profile to pass through to the sample. In preferred embodiments, a substantially flat-top profile is obtained by the use of optical fibers within the illumination system. In a fiber delivery system, various techniques may be used as described below to achieve such a profile. These techniques include: physically modulating the fiber, using tapered fibers, modulating the beam (e.g., by dithering the focus) into the fiber, bending a multimode fiber, and combinations thereof. While bending the fiber is one possible embodiment, the other methods described herein are preferred, since they are less likely to result in fiber breakage.

Figure 6:
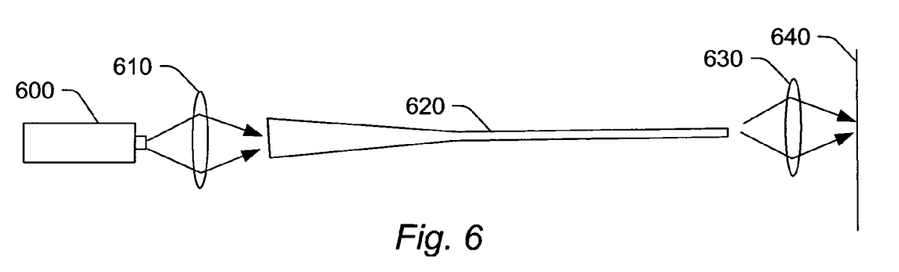
FIGS. 6–9 are schematic diagrams illustrating side views of an energy beam source coupled to different embodiments of an energy beam delivery subsystem.

In accordance with one preferred embodiment, as shown in FIG. 6, the energy beam source includes optical source 600 such as a laser, which is used to provide light for the energy beam. Optical source 600 may include any of the light sources described above. The energy beam delivery subsystem includes coupling optics 610, tapered optical fiber 620, and coupling optics 630. As shown in FIG. 6, coupling optics 610 and 630 may be spherical refractive lenses. However, coupling optics 610 and 630 may include any other optics described herein or any other appropriate coupling optics known in the art.

As shown in FIG. 6, the light generated by optical source 600 passes through coupling optics 610, which is configured to couple the energy beam into fiber 620. In this embodiment, fiber 620 is tapered along its length. The optical fiber also includes a multi-mode optical fiber. Light from fiber 620 then passes through focusing optics 630 and arrives at focal plane 640. Focal plane 640 may coincide with the surface of a sample such as a semiconductor substrate, so that a beam having a substantially flat-top profile can be supplied to the surface and used to clean the surface before measurement of the cleaned region of the surface as described above.

Normally, careful matching of the coupling optics numerical aperture (NA) to the fiber's acceptance NA is required to achieve an optimum mode population. However, such NA matching is not required here. For instance, the result of the fiber taper is an efficient mode population that is more or less independent of the input NA. In particular, as light propagates along the length of the fiber, the fiber diameter decreases. The total number of available spatial modes decreases as the fiber diameter shrinks. Therefore, light that was propagating in the disappearing modes has to be re-distributed among the remaining modes. This redistribution happens continually along the tapered portion of the fiber, so that by the time the fiber has reached its terminal diameter, a well-distributed mode population has been achieved.

The tapered fiber maximizes the uniformity of the exit beam, by efficiently populating the fiber spatial modes in a manner that is largely independent of the input NA. This independence on input NA has a major advantage for coupling pulsed lasers, where optical damage of the fiber is a concern. Since with the tapered fiber it is not crucial to match the fiber NA when coupling an energy beam into the fiber, the coupling NA can be reduced. In one embodiment, therefore, an NA of coupling optics 610 may be less than an input NA of optical fiber 620. Decreasing the NA of the coupling optics allows the spot size of the input beam on the entrance face of the optical fiber to be larger since you do not have to focus as tightly, and the risk of optical fiber damage is decreased since the energy per unit area is decreased. As a result, using the tapered fiber, it is possible to get a full population of fiber modes at higher pulse energies than would be possible otherwise. In addition, irrespective of pulse energy, the population of modes of the fiber is maximized (and hence uniformity as well) in a manner that is insensitive to input coupling. The system embodiment shown in FIG. 6 may be further configured as described herein.

Figure 7:
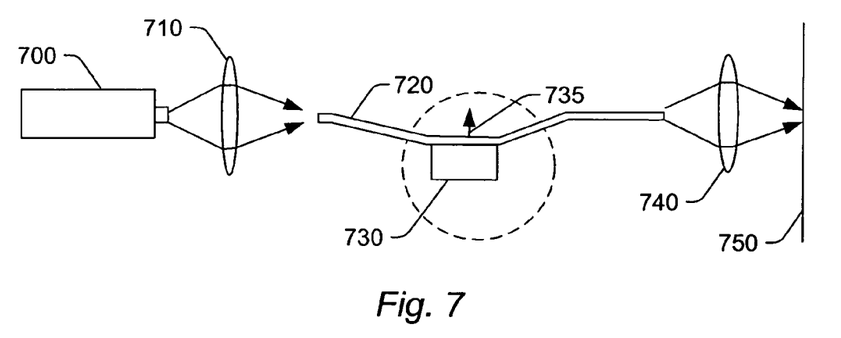

In another embodiment, the energy beam delivery subsystem may include an optical fiber, and the fiber is physically modulated to create the substantially flat-top profile. In this embodiment, as shown in FIG. 7, the energy beam source includes optical source 700 such as a laser, which is used to provide light. Optical source 700 may include any of the other optical sources described herein. The energy beam delivery subsystem includes coupling optics 710, optical fiber 720, modulation device 730, and coupling optics 740. Although coupling optics 710 and 740 are shown to be spherical refractive lenses, it is to be understood that the coupling optics may include any of the optics described herein or any other appropriate coupling optics known in the art. In addition, coupling optics 710 may have an NA that is less than the acceptance NA of the fiber as described further above.

The light from the energy beam source passes through coupling optics 710 and from there into fiber 720. Although fiber 720 is shown to be a non-tapered fiber, it is to be understood that, in some embodiments, fiber 720 may be an optical fiber that is tapered along a length of the optical fiber. In this embodiment, fiber 720 is coupled to modulation device 730, which may be a transducer. The modulation device is configured to physically modulate a position of the optical fiber, for example, in the direction shown by arrow 735. Light from fiber 720 may then pass through focusing optics 740 and arrive at focal plane 750. Focal plane 750 may coincide with the surface of a sample such as a semiconductor substrate, so that a beam having a substantially flat-top profile can be supplied to the surface and used to clean the surface before measurement of the cleaned region of the surface.

In this manner, a standard fiber delivery system can be used, in which optical source 700 is coupled, using appropriate optics 710, into fiber 720 at the entrance face. The intensity profile at the exit face would typically be imaged onto the surface of interest, but for the purpose of monitoring the intensity profile, it may instead if desired be imaged onto a charged-coupled device (CCD) camera or other imaging device, as described further herein.

Modulation device 730 is used to physically modulate fiber 720, in a way that changes the distribution of populated spatial modes. This can be achieved, for example, by attaching fiber 720 to a modulation device such as a voice coil, with the coil driven by a suitable waveform thereby producing a time-varying stress in fiber 720. The effect of this varying stress is to change the populated mode structure of fiber 720, in conjunction with the waveform. This causes a "dithering" of the speckle pattern thereby resulting in a time-averaged intensity profile that is improved in terms of uniformity. The embodiment of the system shown in FIG. 7 may be further configured as described herein.

In yet another embodiment, a time varying coupling of the energy beam into the fiber is provided. This is a corollary to the method described above, but instead of modulating the fiber, the light is modulated so as to cause a modulation in the coupling into the fiber thereby producing a time-varying coupling into the fiber mode structure which produces a similar result (e.g., a time averaged uniform intensity at the exit of the optical fiber). This time-varying intensity can be achieved by using an optically active material in the coupling optics. For example, an acousto optic modulator (AOM) could be used to dither the input focus, and the same effect could be achieved using a electro-optic modulator (EOM) or photoelastic modulator (PEM) in conjunction with a birefringent crystal.

Figure 8:
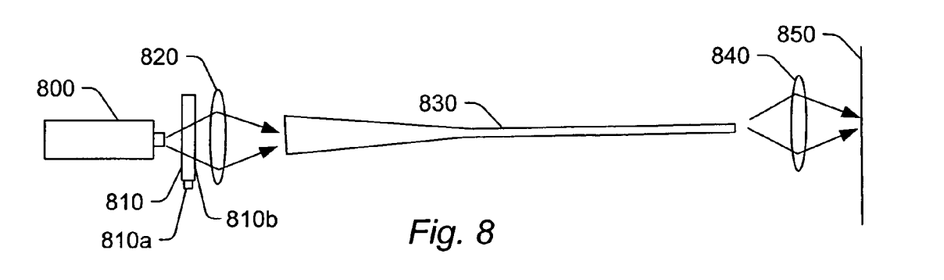

One such embodiment is illustrated in FIG. 8. In this embodiment, the energy beam source includes optical source 800, which may be configured as described above. Optical source 800 is coupled to an energy beam delivery subsystem that includes modulation device 810, coupling optics 820, optical fiber 830, and coupling optics 840. Coupling optics 820 and 840 may be configured as described above. Optical fiber 830 may also be configured as described above. For instance, the optical fiber may be a non-tapered fiber or a tapered fiber.

Light from optical source 800 is directed to modulation device 810. The modulation device is configured to modulate a position of the energy beam directed to the optical fiber. For example, in this embodiment, modulation device 810 is configured as an AOM. In this manner, modulation device 810 includes transducer 810a coupled to solid material 810b. Transducer 810a is configured to apply a sound wave or a "chirp" signal to the solid material to change an optical property of the solid material such as refractive index. The time-varying refractive index causes the light from the optical source to be directed at varying directions to different positions of coupling optics 820. The AOM may include any appropriate AOM known in the art.

In this manner, the AOM, in combination with coupling optics 820, can be used to scan the light across the input face of optical fiber 830. As such, the modulation of the light into the fiber produces a time-varying coupling into the fiber mode structure thereby achieving a time averaged uniform intensity at the exit of the optical fiber. Therefore, the electron beam delivery subsystem modifies the energy beam such that the energy beam has a substantially flat-top profile, which can be focused by coupling optics 840 to focal plane 850. Focal plane 850 may be located proximate the surface of the sample such that the substantially flat-top profile energy beam may be incident on the sample surface to facilitate removal of a portion of a contaminant layer on the sample. The embodiment of the system shown in FIG. 8 may be further configured as described herein.

In still another embodiment, static changes to coupling optics may be used. For example, by using an optical diffuser in the coupling optics, an array of foci can be created at the same focal plane. This produces in a static sense what the time varying (dithering) technique described above achieves. The result will be a more efficient population of the fiber spatial modes.

Figure 9:
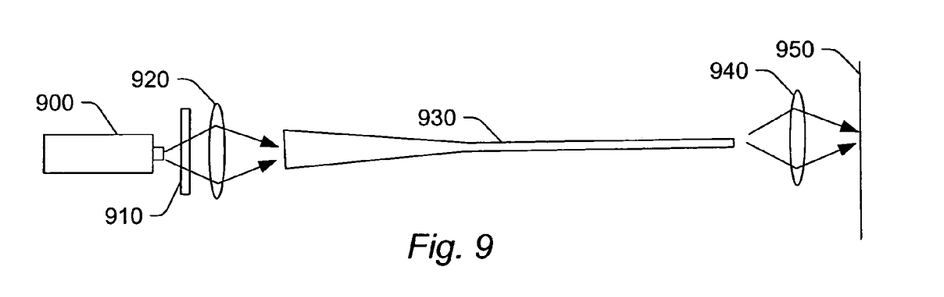

One example of such an embodiment is illustrated in FIG. 9. As shown in FIG. 9, the energy beam source includes optical source 900. Optical source 900 may include any of the light sources described herein. Optical source 900 is coupled to an electron beam delivery subsystem that includes optical diffuser 910, coupling optics 920, optical fiber 930, and coupling optics 940. Coupling optics 920 and 940 may include any of the coupling optics described above. In addition, optical fiber 930 may be configured as described above (e.g., a multi-mode non-tapered fiber or a multi-mode tapered fiber). The optical diffuser may include any appropriate optical diffuser known in the art.

Light from optical source 900 is directed to optical diffuser 910, which is configured to average the intensity of the light from optical source 900 in a static sense as a function of position in the beam profile. As such, the spatial modulation of the light directed into the fiber produces a more uniform coupling into the fiber mode structure thereby achieving a spatially averaged uniform intensity at the exit. Therefore, the electron beam delivery subsystem modifies the energy beam such that the energy beam has a substantially flat-top profile. Light from optical diffuser 910 is directed by coupling optics 920 to an input face of optical fiber 930. Light exiting optical fiber 930 is directed to focal plane 950 by coupling optics 940. As described above, focal plane 950 may be located proximate the surface of the sample such that the substantially flat-top profile energy beam may be incident on the sample surface to facilitate removal of a portion of a contaminant layer on the sample. The embodiment of the system shown in FIG. 9 may be further configured as described herein.

Figure 10:
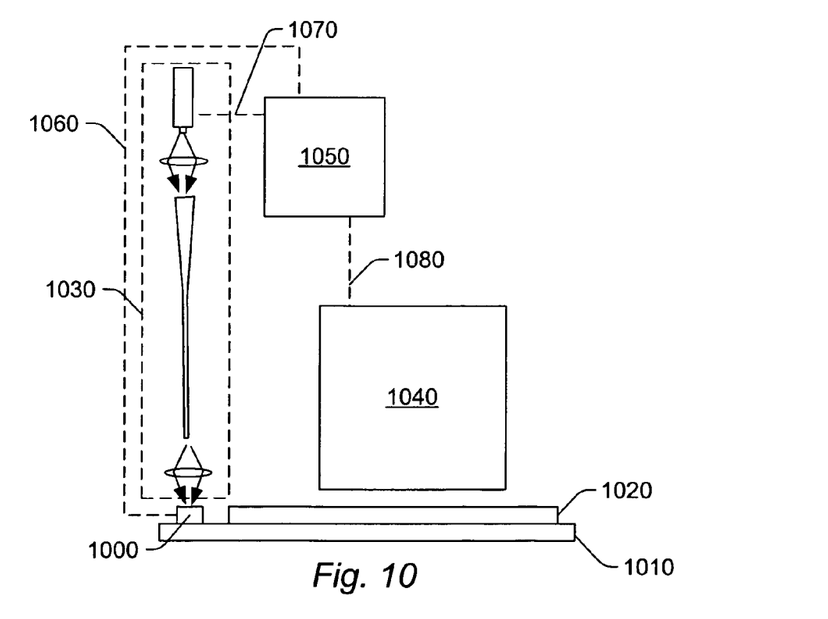
FIG. 10 is a schematic diagram illustrating a side view of one embodiment of a system configured to prepare a sample for thin film analysis, which includes a detector coupled to a stage.

In a preferred embodiment, the system may be configured to check the beam profile. In one embodiment shown in FIG. 10, the system includes detector 1000 coupled to stage 1010. Stage 1010 is configured to support sample 1020. The stage may be used to support the sample during both cleaning and measurement as described above. For example, the system includes system 1030, which is configured to prepare the sample for thin film analysis by removing a portion of a contaminant layer on the sample to expose an analysis area of a thin film on the sample. Although system 1030 is shown to be configured as the system embodiment shown in FIG. 6, it is to be understood that system 1030 may be configured according to any of the embodiments described herein. The system shown in FIG. 10 also includes thin film analysis subsystem 1040. Thin film analysis subsystem 1040 may be configured as described above. As shown in FIG. 10, system 1030 and thin film analysis subsystem 1040 are coupled to the same stage (i.e., a common stage), which provides advantages as described further above.

As shown in FIG. 10, system 1030 may be positioned such that the system can direct light to a focal plane that is coincident with a photosensitive surface of detector 1000. For instance, system 1030 and/or the stage may be configured to move such that a position of system 1030 relative to the stage is altered (e.g., from a position above sample 1020 to a position above detector 1000). Detector 1000 is configured to monitor an intensity of the energy beam as a function of position across the profile. The detector may be further configured as described herein. For example, in one embodiment, the detector may include a single sensing element. In some embodiments, the detector may also be configured to monitor focus of the energy beam on the sample. The detector may perform monitoring of the intensity profile and/or focus of the energy beam as described further herein.

In some embodiments, the system shown in FIG. 10 may include processor 1050. Processor 1050 may be coupled to detector 1000 by transmission medium 1060. Transmission medium 1060 may include "wired" and/or "wireless" portions. Detector 1000 may provide the measured intensity profile and/or focus of the energy beam to the processor across transmission medium 1060. The processor may perform one or more functions depending on the measured intensity profile and/or focus of the energy beam. For instance, if the intensity profile of the energy beam is not within predetermined limits for the intensity profile, the processor may check the status of the optical source to determine if the optical source is turned on. The processor may communicate with the optical source via transmission medium 1070, which may be configured as described above. The processor may also control the optical source via transmission medium 1070 (e.g., to turn the optical source on if the energy beam is to be used for a cleaning operation). In a similar manner, if the focus of the energy beam is not within predetermined limits for the focus, the processor may alter a position of system 1030 and/or stage 1010 to alter the focus of the energy beam, preferably to correct the focus.

The processor may be coupled to other components of the system such as thin film analysis subsystem 1040, for example, by transmission medium 1080, which may be configured as described above. In this manner, the processor may be configured to perform one or more functions on measurement data produced by the thin film analysis subsystem (e.g., determine a thickness of the thin film on sample 1020). The processor may include any suitable processor or computer system known in the art. The system shown in FIG. 10 may be further configured as described herein.

In one such embodiment, the system may include a detector with small sensing element(s), mechanical attachment to the moving stage, electronics amplifier and gain control, data acquisition software and positioning, beam profile, and intensity calibrations algorithm. The detector can be a single photo-diode or an optical sensor array. The detector preferably has high sensitivity at the wavelength region covering all optical beams that are to be tested. For a detector of a single sensing element, to obtain high spatial resolution, the size of the sensing area is relatively small. A typical spatial resolution is about 3 μm to about 10 μm. This spatial resolution requires the size of the sensing element to be about 3 μm to about 10 μm as well.

An alternate way to achieve the same spatial resolution is to use a small size aperture in front of a detector that has a relatively large sensing area. In that case, there is an NA consideration to be made in selecting an appropriate detector. In particular, the NA of the detector should be greater than the NA of the beam to be measured.

The detector can also be a one-dimensional or two-dimensional array detector. Array sensors can enhance measurement speed. Besides higher cost, the disadvantages of the array detectors are the size (relatively large) and the cross-element sensitivity calibration. In addition, the detector is installed on the moving stage at a location that can be reached by all optical beams that are to be measured within the stage moving range. A miniature sized detector with a single sensing element is particularly suitable for metrology tools that have relatively little available space inside.

To measure beam profile and focus for a particular beam in the metrology tool (e.g., the energy beam and/or the probe beam), the following process may be used. First, move the detector to the location of the beam. This initial location may be calculated from parameters of the mechanical design and accounting for a certain tolerance. The detector is scanned at the plane perpendicular to the beam. Assume this plane is the X-Y plane. The span of the x-y scan range is preferably big enough (usually at least twice the mechanical tolerance for the beam location) in order to find the beam. The step of the scan can be adjusted. At each step, the signal from the detector and amplifier is recorded. When the scan is finished, the matrix of the data is processed. The center of the beam can be determined by using different models. After finding the coarse position of the beam center, the detector is moved to the center of the beam. A fine x-y scan is then performed. The fine scan gives the beam spatial intensity profile at that plane.

To determine the focal plane of the beam and the beam intensity profile at the focal plane, a z-scan of the energy beam by the detector followed by an x-y scan can be performed. To obtain accurate measurement for focal plane and beam profile at focal plane, iteration of z-scan and x-y scan may performed until there is no meaningful improvement on the measurement. The offset between foci of different optical subsystems can be determined by subtracting the measured beam coordinates between two optical subsystems. The detector can be calibrated for intensity measurement of the beam image plane as well.

The various embodiments described above may be used in combination, if desired, to achieve a substantially flat-top profile. In addition, one or more of the embodiments described above may be used to perform a method for preparing a sample for thin film analysis. In particular, the embodiments described herein may be used to generate an energy beam and to modify the energy beam such that the energy beam has a substantially flat-top profile. The method also includes directing the energy beam to the sample. The energy beam is configured to remove a portion of a contaminant layer on the sample to expose an analysis area of a thin film on the sample.

In one embodiment, modifying the energy beam includes physically modulating a position of an optical fiber along which the energy beam is traveling, which may be performed as shown in FIG. 7. In another embodiment, modifying the energy beam includes modulating a position of the energy beam directed to an optical fiber, which may be performed as shown in FIG. 8. In an additional embodiment, the method may include monitoring intensity of the energy beam as a function of position across the profile, which may be performed as shown in FIG. 10. As further shown in FIG. 10, the sample may be disposed on a stage during generation of the energy beam, modification of the energy beam and direction of the energy beam to the sample by system 1030. In one such embodiment, the method may also include performing the thin film analysis of the analysis area while the sample is disposed on the stage using thin film analysis subsystem 1040. Each of the embodiments described above may include any other step(s) described herein.

Further modifications and alternative embodiments of various aspects of the invention may be apparent to those skilled in the art in view of this description. For example, methods and systems for preparing a sample for thin film analysis are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to prepare a sample for thin film analysis, comprising:
   an energy beam source configured to generate an energy beam; and
   an energy beam delivery subsystem configured to direct the energy beam to the sample and to modify the energy beam such that the energy beam has a substantially flat-top profile on the sample, wherein the energy beam is configured to remove a portion of a contaminant layer on the sample to expose an analysis area of a thin film on the sample.

2. The system of claim 1, wherein the energy beam source comprises a laser.

3. The system of claim 1, wherein the energy beam delivery subsystem comprises a multi-mode optical fiber.

4. The system of claim 1, wherein the energy beam delivery subsystem comprises an optical fiber that is tapered along a length of the optical fiber.

5. The system of claim 1, wherein the energy beam delivery subsystem comprises an optical fiber that is tapered along a length of the optical fiber and coupling optics configured to couple the energy beam into the optical fiber, and wherein a numerical aperture of the coupling optics is less than an input numerical aperture of the optical fiber.

6. The system of claim 1, wherein the energy beam delivery subsystem comprises an optical fiber coupled to a modulation device, and wherein the modulation device is configured to physically modulate a position of the optical fiber.

7. The system of claim 6, wherein the optical fiber comprises an optical fiber that is tapered along a length of the optical fiber.

8. The system of claim 1, wherein the energy beam delivery subsystem comprises an optical fiber and a modulation device, and wherein the modulation device is configured to modulate a position of the energy beam directed to the optical fiber.

9. The system of claim 1, wherein the energy beam delivery subsystem comprises an optical fiber coupled to coupling optics, wherein the coupling optics are configured to couple the energy beam into the optical fiber, and wherein the coupling optics comprise an optical diffuser.

10. The system of claim 1, further comprising a detector coupled to a stage, wherein the detector is configured to monitor intensity of the energy beam as a function of position across the profile, and wherein the stage is configured to support the sample.

11. The system of claim 10, wherein the detector comprises a single sensing element.

12. The system of claim 10, wherein the detector is further configured to monitor focus of the energy beam on the sample.

13. The system of claim 1, further comprising a thin film analysis subsystem, wherein the thin film analysis subsystem and the energy beam delivery subsystem are coupled to a common stage.

14. The system of claim 1, wherein the substantially flat-top profile has an approximately constant intensity across the profile of the energy beam.

15. A method for preparing a sample for thin film analysis, comprising:
 generating an energy beam;
 modifying the energy beam such that the energy beam has a substantially flat-top profile; and
 directing the energy beam to the sample, wherein the energy beam is configured to remove a portion of a contaminant layer on the sample to expose an analysis area of a thin film on the sample.

16. The method of claim 15, wherein said modifying comprises physically modulating a position of an optical fiber along which the energy beam is traveling.

17. The method of claim 15, wherein said modifying comprises modulating a position of the energy beam directed to an optical fiber.

18. The method of claim 15, further comprising monitoring intensity of the energy beam as a function of position across the profile.

19. The method of claim 15, wherein the substantially flat-top profile has an approximately constant intensity across the profile of the energy beam.

20. The method of claim 15, wherein the sample is disposed on a stage during said generating, modifying, and directing, and wherein the method further comprises performing the thin film analysis of the analysis area while the sample is disposed on the stage.

* * * * *